United States Patent [19]
Drivon et al.

[11] Patent Number: 5,981,815
[45] Date of Patent: Nov. 9, 1999

[54] METHOD FOR PREPARING α, ω-BROMOCHLOROALKANES

[75] Inventors: Gilles Drivon, Saint-Martin-en-Haut; Christophe Ruppin, Pierre-Bènite, both of France

[73] Assignee: ELF Atochem, S.A., Paris, France

[21] Appl. No.: 08/981,953

[22] PCT Filed: Jul. 3, 1996

[86] PCT No.: PCT/FR96/01036

§ 371 Date: May 5, 1998

§ 102(e) Date: May 5, 1998

[87] PCT Pub. No.: WO97/03037

PCT Pub. Date: Jan. 30, 1997

[30] Foreign Application Priority Data

Jul. 11, 1995 [FR] France .................................. 95 08361

[51] Int. Cl.$^6$ .............................. C07C 17/00; C07C 19/00
[52] U.S. Cl. ........................... 570/241; 570/259; 570/261
[58] Field of Search .................................... 570/241, 259, 570/261

[56] References Cited

U.S. PATENT DOCUMENTS

| | | | |
|---|---|---|---|
| 2,218,018 | 10/1940 | Cass | 570/259 |
| 2,852,532 | 9/1958 | Hamel | 570/259 |
| 3,406,212 | 10/1968 | Christie et al. | 570/259 |

*Primary Examiner*—Alan Siegel
*Attorney, Agent, or Firm*—Millen, White, Zelano & Branigan, P.C.

[57] ABSTRACT

The invention relates to a process for the preparation of α,ω-bromochloroalkanes. A cyclic ether is hydrobrominated and then the phase obtained is reacted, without any prior purification or separation, with thionyl chloride.

18 Claims, No Drawings

METHOD FOR PREPARING α, ω-BROMOCHLOROALKANES

This application is a 371 of PCT/FR 96/01036 filed Jul. 3,1996.

The present invention relates to a process for the direct preparation of α,ω-bromochloroalkanes from cyclic ethers.

Haloalkanes, and more particularly α,ω-bromochloroalkanes, are widely used as starting reactants for the preparation of pharmaceutical, pesticidal and detergent products.

Many methods have been described for producing these α,ω-bromochloroalkanes.

They most often involve the reaction of halogens (bromine or chlorine) or of their derivatives, such as $PBr_3$ or $SBr_6$, with an α,ω-chlorohydroxyalkane or alternatively the reaction of halogens (bromine or chlorine) or of their derivatives, such as $SOCl_2$, with a haloalkane or an ω-haloalkanoic acid.

British Patent 788,349 describes a process for the preparation of 1-bromo-4-chlorobutane which consists in treating, in a first stage, THF with dry hydrochloric acid in the presence of traces of $ZnCl_2$ at a temperature which reaches approximately 100° C. and then, in a second stage, in treating the 4-chloro-1-butanol obtained above with red phosphorus and then with dry bromine at a temperature of between 0° C. and −10° C. The 1-bromo-4-chlorobutane is obtained with a yield of approximately 62% with respect to the TEF used.

U.S. Pat. No. 2,839,574 mentions a process for the preparation of 1-bromo-4-chlorobutane which avoids the use of red phosphorus and of bromine or of $SBr_6$. This process consists in treating predistilled 4-chloro-1-butanol with dry gaseous hydrobromic acid in the presence of a solvent at boiling point which forms an azeotrope with the water formed according to the reaction:

$$Cl(CH_2)_4OH + HBr \longrightarrow Br(CH_2)_4Cl + H_2O.$$

The yield is approximately 70%.

In the Japanese patent application published under No. JP 5791930, the 1-bromo-4-chlorobutane was obtained with a yield of approximately 90% by treating freshly distilled 4-chloro-1-butanol with $SBr_6$ formed from sulphur and bromine, according to the reaction scheme:

$$SBr_6 + 6\ Cl(CH_2)_4OH \rightarrow 6\ Br(CH_2)_4Cl + H_2SO_4 + 2H_2O$$

In the case where $SBr_6$ is reacted with an unpurified 4-chloro-1-butanol, arising in particular from a mixture of tetrahydrofuran and hydrochloric acid, the 1-bromo-4-chlorobutane yield is approximately 70%.

D. C. Sayles and Ed. F. Degering (Journal of American Chemistry Society, 71, page 3162, 1949) describe a method for the preparation of 1-bromo-4-chlorobutane by treating n-bromobutane with sulphuryl chloride ($SO_2Cl_2$) in the presence of benzoyl peroxide, at reflux of the reactants. The 1-bromo-4-chlorobutane yield is 35%.

Smushkevich, Yu. I et al. apply the Borodin-Hunsdiecker reaction to ω-chloroalkanoic acids (Tr. Mosk. Khim. Technol. Inst. No. 61, pp 47–48, 1969).

They thus obtain α,ω-bromochloroalkanes by treating ω-chloroalkanoic acids with HgO and bromine in $CCl_4$ medium according to the reaction scheme:

$$Cl(CH_2)_nCOOH + Br_2 \rightarrow Cl(CH_2)_nBr + CO_2 + HBr$$

All these methods have many disadvantages. They use starting compounds which are often impure, requiring purification operations, and reactants which are expensive and difficult to handle (P+bromine, S+bromine).

The α,ω-bromochloroalkane yields are low and the products obtained contain impurities, the removal of which results in difficult and expensive separation operations.

A process has now been found for the direct preparation of α,ω-bromochloroalkanes of formula $$Br(CH_2)_nCl \quad (I)$$

in which n represents an integer ranging from 3 to 8, from a cyclic ether of formula $$\text{(II)}$$

$$\underset{O}{\underbrace{(CH_2)_n}}$$

in which n has the same meaning as in the formula (I), characterized in that:

a) the said cyclic ether (II) is brought into contact with gaseous hydrobromic acid and then b) the phase obtained above in a) is brought into contact with thionyl chloride ($SOCl_2$) and a compound containing an N-alkylated or N-dialkylated carboxylic acid amide group.

Mention may be made, as an example of a cyclic ether (II) which can be used according to the present invention, of 1,3-propylene oxide (oxetane), tetrahydrofuran, tetrahydropyran, 1,6-hexamethylene oxide (oxepane) or 1,7-heptamethylene oxide (oxocane).

The process of the present invention applies very particularly to the preparation of 1-bromo-4-chlorobutane from tetrahydrofuran.

Mention will be made, by way of illustration of compounds containing an N-alkylated or N-dialkylated carboxylic acid amide group which can be used according to the present invention, of N-methylacetamide, dimethylformamide or diethylformamide.

It is preferable, among these compounds, to use dimethylformamide.

Use will be made of amounts by weight of these compounds at most equal to 5% with respect to the ether used and preferably of amounts by weight of between 0.1% and 3%.

According to the present invention, it is not necessary to isolate and/or to purify the α,ω-bromohydroxyalkane (III) obtained in a) by hydrobromination of the cyclic ether (II) according to the reaction scheme:

$$\underset{(II)}{\underbrace{(CH_2)_n}_{O}} + HBr \longrightarrow \underset{(III)}{HO(CH_2)_nBr} \quad (A)$$

The stage b) is carried out by bringing the phase obtained above in a), which contains the intermediate (III), directly into contact with thionyl chloride and a compound containing an N-alkylated or N-dialkylated carboxylic acid amide group, to result in the α,ω-bromochloroalkane (I) according to the reaction scheme:

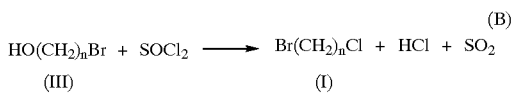

(B)

One of the advantages of the invention is clearly apparent here; it is not necessary to isolate and/or purify the α,ω-bromohydroxyalkane (III) formed as an intermediate in the stage a) before bringing it into contact with the thionyl chloride (stage b).

The process according to the invention can be carried out at temperatures ranging from approximately 0C. to 30° C. for the stage a) and from approximately 20° C. to 130° C., and preferably from 50° C. to 700° C., for the stage b).

A temperature greater than 30° C. in the stage a) would be liable to lower the content of intermediate compound (III) and to result in the formation of undesirable side products, such as dibromoalkanes.

The process is carried out with an HBr/cyclic ether ratio virtually equal to 1 and an $SOCl_2$/cyclic ether ratio of between 0.90 and 1.50 and preferably of between 0.95 and 1.20.

The duration of the stages a) and b) can vary within wide limits but is generally between 5 hours and 20 hours and preferably between 10 and 15 hours.

The reaction can be carried out at atmospheric pressure. According to one way of carrying out the process, gaseous hydrobromic acid is introduced with stirring into the cyclic ether. On completion of the introduction, unreacted hydrobromic acid is optionally degassed from the reaction mixture under reduced pressure or by entraining with an inert gas, such as nitrogen, and preferably at room temperature. Then, after having introduced a compound containing an N-alkylated or N-dialkylated carboxylic acid amide group, thionyl chloride is added.

The hydrochloric acid and the sulphur dioxide formed continuously degas from the reaction mixture.

This degassing can be promoted, in particular at the end of the reaction, by sweeping with an inert gas or alternatively by placing the reaction mixture under reduced pressure.

The hydrochloric acid and the sulphur dioxide removed can then be neutralized in one or a number of absorption columns containing sodium hydroxide and an alkaline sulphite, such as, for example, sodium sulphite.

It would not be departing from the scope of the invention if the stage b) were carried out in the absence of a compound containing an N-alkylated or N-dialkylated carboxylic acid amide group.

The preparation of α,ω-bromochloroalkanes according to the process of the invention has the advantage of being carried out in two successive reaction stages in the same equipment, without any purification or separation of the intermediate α,ω-bromohydroxyalkane.

Another advantage of the process according to the invention is that of being carried out without solvent.

The α,ω-bromochloroalkane yields are high and the products obtained are purified by methods known to the person skilled in the art, such as distillation.

The examples which follow illustrate the invention.

EXAMPLE 1

Stage a 216 g of tetrahydrofuran (THF), i.e. 3 mol, are introduced at room temperature into a 1 liter reactor, surmounted by a colunn packed with Raschig rings and by a condenser cooled to −25° C., equipped with a stirrer, a temperature controller and a jacket in which a thermal liquid circulates and then, with stirring, gaseous hydrobromic acid is injected into the base of the reactor at a flow rate of 1 mol/h for 2 hours and then, subsequently, at a flow rate of 0.5 mol/h for 2 hours, while maintaining the temperature of the reaction mixture at room temperature (approximately 20° C.).

Analysis by gas phase chromatography (GPC) of the reaction phase obtained shows that it contains 91% by weight of 4-bromo-1-butanol, 5% by weight of 1,4-dibromobutane and 4% by weight of unconverted THF.

The 4-bromo-l-butanol crude molar yield is equal to 88% with respect to the THF used.

Stage b 0.84 g of dimethylformamide is introduced into the phase a) obtained above. The reaction mixture is brought to 50° C. and then 357 g of $SOCl_2$, i.e. 3 mol, are run in with stirring over 90 minutes, while maintaining the temperature at 50° C. On completion of the addition of $SOCl_2$, the temperature of the reaction mixture is raised to 70° C., which temperature is maintained for 2 hours; the hydrochloric acid and the $SO_2$ formed which degas continuously are neutralized by means of an absorption colulmn containing a mixture of sodium hydroxide and sodium sulphite.

After cooling to room temperature, the reaction mixture is washed with 105 g of water and then settled. 504 g of an organic phase are obtained, which phase contains 84.7% by weight of 1-bromo-4-chlorobutane, 9.3% by weight of 1,4-dibromobutane, 2.5% by weight of 1,4-dichlorobutane and 1.9% of THF, i.e. a 1-bromo-4-chlorobutane crude molar yield of 83% with respect to the THF used.

The organic phase is subjected to distillation under a reduced pressure of 25 mm Hg in an adiabatic column containing 30 theoretical plates.

The 1-bromo-4-chlorobutane is obtained (B.p.$_{25\ mm\ Hg}$ =76° C./76.5° C.) with a purity greater than 99.5%. The distillation yield is of the order of 75%.

EXAMPLE 2

The operating conditions of the stages a) and b) are identical with those of the stages a) and b) of Example 1, except that the $SOCl_2$ is run in at 70° C. instead of 50° C.

A reaction mixture is obtained (before purification) which is composed of:

73.2% by weight of 1-bromo-4-chlorobutane, 15.7% by weight of 1,4-dibromobutane, 6% by weight of 1,4-dichlorobutane, 2.4% by weight of THF.

A 1-bromo-4-chlorobutane crude molar yield of 70.5% with respect to the THF used is obtained. The reaction mixture is treated as in Example 1 and the organic phase is subjected to distillation under reduced pressure.

EXAMPLE 3

The process is carried out as in Example 2, except that, in the stage b), the $SOCl_2$ is added at a temperature of 60° C. instead of 70° C.

A reaction mixture is obtained (before purification) which is composed of:

81% by weight of 1-bromo-4-chlorobutane, 11.5% by weight of 1,4-dibromobutane,

4% by weight of 1,4-dichlorobutane, 1.3% by weight of THF.

A 1-bromo-4-chlorobutane crude molar yield of 78% is obtained.

EXAMPLE 4

Not in Accordance with the Invention

The stage a) is carried out with amounts of reactants identical with Example 1 but according to different operating conditions. The temperature is 67° C at the beginning of the injection of HBr and the temperature is 105° C. at the end of the injection of HBr.

Analysis by GPC of the reaction phase shows that it contains 52% by weight of 4-bromo-1-butanol, 36% by weight of 1,4-dibromobutane and 12% by weight of THF. This corresponds to a 4-bromo-1-butanol molar yield of approximately 50% with respect to the THF used.

EXAMPLE 5

Stare a)

This stage a) is carried out according to operating conditions identical with those of the stage a) of Example 1, except that 8 mol of THF and 8 mol of HBr are used, the HBr being introduced at a flow rate of 1.5 mol/h for 5 hours and then at a flow rate of 1 mol/h for 30 minutes.

Stage b)

9.5 mol of $SOCl_2$ (18.7% molar excess with respect to the THF used) are run in directly at 50° C. for 4 hours and heating is then carried out for 2h 30 at 65° C.–85° C. and for 2 hours at 130° C.

After cooling, the reaction mixture is washed with water and settled.

Analysis by GPC of the organic phase which has settled out shows that the 1-bromo-4-chlorobutane has been obtained with a crude molar yield of 77.5% with respect to the THF used.

We claim:

1. A process for the direct preparation of α,ω-bromochloroalkanes of formula

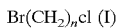

in which n represents an integer ranging from 3 to 8, from a cyclic ether of formula

 (II)

in which n has the same meaning as in the formula (I), characterized in that:

a) the said cyclic ether (II) is brought into contact with gaseous hydrobromic acid and then b) the phase obtained above in a) is brought into contact with thionyl chloride ($SOCl_2$) and a compound containing an N-alkylated or N-dialkylated carboxylic acid amide group.

2. A process according to claim 1, characterized in that the cyclic ether (II) is tetrahydrofuran.

3. A process according to claim 1, characterized in that the compound containing an N-dialkylated carboxylic acid amide group is dimethylformamide.

4. A process according to claim 1, characterized in that the compound containing an N-alkylated or N-dialkylated carboxylic acid amide group is used in an amount by weight at most equal to 5% with respect to the cyclic ether.

5. A process according to claim 1, characterized in that the gaseous hydrobromic acid/cyclic ether molar ratio is virtually equal to 1.

6. A process according to claim 1, characterized in that the thionyl chloride/cyclic ether molar ratio is between 0.90 and 1.50.

7. A process according to claim 6, characterized in that the thionyl chloride/cyclic ether molar ratio is between 0.95 and 1.20.

8. A process according to claim 1, characterized in that the temperature of the stage a) ranges from 0°C to 30° C.

9. A process according to claim 1, characterized in that the temperature of the stage b) ranges from 20° C. to 130° C.

10. A process according to claim 9, characterized in that the temperature of the stage b) ranges from 50° to 70° C.

11. A process according to claim 8, characterized in that the temperature of the stage b) ranges from 50° C. to 70° C.

12. A process according to claim 4, wherein said amount by weight is between 0.1% and 3%.

13. A process according to claim 2, characterized in that the compound containing an N-dialkylated carboxylic acid amide group is dimethylformamide.

14. A process according to either claim 13, characterized in that the compound containing an N-alkylated or N-dialkylated carboxylic acid amide group is used in an amount by weight at most equal to 5% with respect to the cyclic ether.

15. A process according to claim 14, characterized in that the gaseous hydrobromic acid/cyclic ether molar ratio is virtually equal to 1.

16. A process according to claim 1, characterized in that the thionyl chloride/cyclic ether molar ratio is between 0.90 and 1.50.

17. A process according to claim 16, characterized in that the temperature of the stage a) ranges from 0° C. to 30° C.

18. A process according to claim 17, characterized in that the temperature of the stage b) ranges from 50° C. to 70° C.

* * * * *